(12) United States Patent
Kim et al.

(10) Patent No.: US 11,883,483 B2
(45) Date of Patent: Jan. 30, 2024

(54) METHOD FOR PREPARING INFLUENZA WORKING VIRUS SEED STOCK, METHOD FOR PREPARING INFLUENZA VACCINE USING SAME SEED STOCK, AND VIRUS SEED STOCK PREPARED BY SAME METHOD

(71) Applicant: SK BIOSCIENCE CO., LTD., Seongnam-Si (KR)

(72) Inventors: Yun Hee Kim, Seongnam-Si (KR); Yong Wook Park, Suwon-Si (KR); Dong Soo Ham, Suwon-Si (KR); Hwan Ui Jung, Seoul (KR); Hun Kim, Suwon-Si (KR)

(73) Assignee: SK BIOSCIENCE CO., LTD., Seongnam-si (KR)

( * ) Notice: Subject to any disclaimer, the term of this patent is extended or adjusted under 35 U.S.C. 154(b) by 0 days.

(21) Appl. No.: 16/628,228

(22) PCT Filed: Jul. 5, 2018

(86) PCT No.: PCT/KR2018/007630
§ 371 (c)(1),
(2) Date: Jan. 2, 2020

(87) PCT Pub. No.: WO2019/009640
PCT Pub. Date: Jan. 10, 2019

(65) Prior Publication Data
US 2021/0060153 A1 Mar. 4, 2021

(30) Foreign Application Priority Data
Jul. 5, 2017 (KR) .................. 10-2017-0085472

(51) Int. Cl.
*A61K 39/145* (2006.01)
*A61P 31/16* (2006.01)

(52) U.S. Cl.
CPC ............ *A61K 39/145* (2013.01); *A61P 31/16* (2018.01)

(58) Field of Classification Search
None
See application file for complete search history.

(56) References Cited

U.S. PATENT DOCUMENTS

| 10,017,743 | B2 | 7/2018 | Hwang et al. |
| 2003/0044962 | A1 | 3/2003 | Makizumi et al. |
| 2012/0088228 | A1 | 4/2012 | Asher et al. |
| 2013/0183741 | A1 | 7/2013 | Park et al. |
| 2016/0108367 | A1 | 4/2016 | Hwang et al. |

FOREIGN PATENT DOCUMENTS

| CN | 103154238 A | 6/2013 |
| CN | 105378072 A | 3/2016 |
| JP | 2016-520329 A | 7/2016 |
| KR | 10-2009-0057015 A | 6/2009 |
| KR | 10-2010-0045436 A | 5/2010 |
| KR | 10-2015-0056519 A | 5/2015 |
| WO | 94/27607 A1 | 12/1994 |
| WO | 2008/032219 A2 | 3/2008 |
| WO | 2009/155168 A1 | 12/2009 |
| WO | 2012/058492 A2 | 5/2012 |
| WO | 2017/072744 A1 | 5/2017 |

OTHER PUBLICATIONS

Abdoli et al., Comparison between MDCK and MDCK-SIAT1 cell lines as preferred host for cell culture-based influenza vaccine production, 2016, Biotechnology Letters, vol. 38, pp. 941-948.*
Huang et al., Serum-Free Suspension Culture of MDCK Cells for Production of Influenza H1N1 Vaccines, 2015, PLoS One, vol. 10, No. 11.*
Milián et al., "Accelerated mass production of influenza virus seed stocks in HEK-293 suspension cell cultures by reverse genetics," *Vaccine* 35:3423-3430, 2017.
Paillet et al., "Statistical optimization of influenza H1N1 production from batch cultures of suspension Vero cells (sVero)," *Vaccine* 29:7212-7217, 2011.
Xue et al., "Propagation and Characterization of Influenza Virus Stocks That Lack High Levels of Defective Viral Genomes and Hemagglutinin Mutations," *Frontiers in Microbiology* 7(Article 326):1-15, Mar. 2016.
Li, et al., "Screening of the High-Yield Influenza B Virus on MDCK Cell and Cloning of its Whole Genome," Chinese Journal of Virology, 20(3), Sep. 2004, 5 pages.

* cited by examiner

*Primary Examiner* — Benjamin P Blumel
(74) *Attorney, Agent, or Firm* — Seed IP Law Group LLP

(57) ABSTRACT

The present invention relates to a method of preparing an influenza working virus seed stock, a method of increasing infectivity of an influenza working virus seed stock, a method of preparing an influenza vaccine using the seed stock, an influenza vaccine prepared by the method, and an influenza working virus seed stock having increased infectivity.

12 Claims, No Drawings

METHOD FOR PREPARING INFLUENZA WORKING VIRUS SEED STOCK, METHOD FOR PREPARING INFLUENZA VACCINE USING SAME SEED STOCK, AND VIRUS SEED STOCK PREPARED BY SAME METHOD

TECHNICAL FIELD

The present invention relates to a method of preparing an influenza working virus seed stock, a method of increasing the infectivity of an influenza working virus seed stock, a method of producing an influenza vaccine using a seed stock prepared by the preparation method, an influenza vaccine produced by the production method, and an influenza working virus seed stock with increased infectivity prepared by the preparation method.

BACKGROUND ART

Influenza viruses are RNA viruses that belong to the family Orthomyxoviridae and have enveloped virions measuring between 80 and 120 nm in diameter. Influenza viruses exist in three types designated A, B, and C. Influenza A viruses are infectious for pigs, horses, humans, birds, and other animals and influenza B and C viruses are infectious only for humans. Influenza A viruses are sub-divided into combinations of 18 different hemagglutinin (HA) subtypes and 11 different neuraminidase (NA) subtypes. Subtypes of influenza B and C viruses remain unknown.

Influenza viruses as RNA viruses mutate more rapidly and frequently than DNA viruses. Accordingly, unlike other vaccines, influenza vaccines for inoculation are newly formulated every year using vaccine strains recommended by the WHO. Such seasonal influenza viruses are usually categorized into A/H1N1, A/H3N2, B/Yamagata, and B/Victoria according to their serum type. Aside from this, when antigenicity is altered by mutation, a new influenza virus emerges to infect people who are not immune, causing a global pandemic. This infectious influenza virus is called a pandemic influenza virus. WHO monitors H5 and H7 subtypes as potentially pandemic viruses.

WHO reports and distributes seasonal and potentially pandemic influenza virus vaccine strains, so that vaccine manufacturers can produce influenza vaccines using the vaccine strains. Such vaccine strains are prepared by a number of techniques such as wild type, reassortment, and reverse genetics. Using the prepared vaccine strains, vaccine manufacturers prepare influenza working virus seed stocks. Thus, there is a need to develop a method of preparing an influenza working virus seed stock with high infectivity in an amount sufficient for use in different batches.

When it is desired to prepare an influenza working virus seed stock using cell culture, cells are usually infected with a virus within a certain range of multiplicity of infection (MOI). MOI is the ratio of an infectious virus to infected cells and is determined through plaque assay for measuring the infectivity of the influenza virus. Plaque assay usually takes 3 days to 7 days to complete. In hemagglutination assay (hereinafter referred to simply as "HA assay"), a virus having a high HA titer is selected. In plaque assay, after comparison of plaque-forming unit (PFU) titers, a virus having the highest PFU titer is selected.

DISCLOSURE

Technical Problem

One object of the present invention is to provide a method of preparing an influenza working virus seed stock that has improved infectivity compared to the originally-received virus and a method of efficiently producing an influenza vaccine using a seed stock prepared by the preparation method in a short time.

Another object of the present invention is to reduce the time and cost required to produce an influenza vaccine, achieving enhanced production efficiency.

Technical Solution

One aspect of the present invention relates to a method of preparing an influenza working virus seed stock, comprising infecting a cell line adapted to serum-free culture and suspension culture with an influenza vaccine virus, culturing the infected cell line, and further passaging the virus culture in the same cell line wherein a culture with a dilution factor where the highest cell viability is obtained is selected from cultures with different dilution factors used for viral infection of the passage, provided that when the hemagglutination assay (HA) titers (except for 0) of two or more cultures are different by 4 times or more, a culture with a dilution factor where the highest HA titer is obtained is selected and used for the subsequent passage.

Another aspect of the present invention relates to a method of increasing the infectivity of an influenza working virus seed stock, comprising infecting a cell line adapted to serum-free culture and suspension culture with an influenza vaccine virus, culturing the infected cell line, and further passaging the virus culture in the same cell line to prepare an influenza working virus seed stock wherein a culture with a dilution factor where the highest cell viability is obtained is selected from cultures with different dilution factors used for viral infection of the passage, provided that when the hemagglutination assay (HA) titers (except for 0) of two or more cultures are different by 4 times or more, a culture with a dilution factor where the highest HA titer is obtained is selected and used for the subsequent passage.

A further aspect of the present invention relates to a method of producing an influenza vaccine, comprising producing an influenza working virus seed stock prepared by the corresponding aspect or an influenza working virus seed stock with increased infectivity by the corresponding aspect on a large scale and attenuating or inactivating the virus seed stock.

Yet another aspect of the present invention relates to an influenza working virus seed stock with increased infectivity prepared by the corresponding method or an influenza vaccine produced by the corresponding method.

Advantageous Effects

The method according to one aspect of the present invention can provide an influenza working virus seed stock in an efficient manner in a short time without the need for plaque assay for measuring the infectivity of the influenza virus.

The method according to one aspect of the present invention can provide an influenza working virus seed stock with increased infectivity compared to the originally-received influenza virus, enabling mass production of an influenza vaccine at low cost in a short time, which is economically advantageous.

MODE FOR INVENTION

One aspect of the present invention relates to a method of preparing an influenza working virus seed stock, comprising infecting a cell line adapted to serum-free culture and suspension culture with an influenza vaccine virus, culturing the infected cell line, and further passaging the virus culture in the same cell line wherein a culture with a dilution factor where the highest cell viability is obtained is selected from cultures with different dilution factors used for viral infection, provided that when the hemagglutination assay (HA) titers (except for 0) of two or more cultures are different by 4 times or more, a culture with a dilution factor where the highest HA titer is obtained is selected and used for the subsequent passage.

As used herein, the expression "cell line adapted to serum-free culture and suspension culture" refers to a cell line that is adapted to a medium substantially free of serum and suspension culture in a state in which a carrier is substantially absent. The "substantially free of serum" means that the serum content is 0.5 v/v % or less, specifically 0.2 v/v % or less, more specifically 0.01 v/v % or less, or no serum is present. The "carrier is substantially absent" means that the carrier content is 0.5 v/v % or less, specifically 0.2 v/v % or less, more specifically 0.01 v/v % or less or no carrier is present. The "adapted" cell line refers to a cell line capable of proliferating in serum-free culture and suspension culture.

The cell line adapted to serum-free culture and suspension culture may be, for example, an MDCK cell line, specifically, MDCK B-702, MDCK KCLRF-BP-00297, MDCK Sky1023 (DSM ACC3112), MDCK Sky10234 (DSM ACC3114) or MDCK Sky3851 (DSM ACC3113), more specifically MDCK Sky1023 (DSM ACC3112), MDCK Sky10234 (DSM ACC3114) or MDCK Sky3851 (DSM ACC3113) which were deposited pursuant to, and in satisfaction of, the requirements of the Budapest Treaty with Deutsche Sammlung von Mikroorganismen und Zellkulturen GmbH (DSMZ GmbH) at Inhoffenstraβe 7 B, 38124 Braunschweig, Germany on Jan. 27, 2011. The passage culture of the virus in the cell line leads to an increase in the infectivity of the virus compared to that of the originally-received virus.

The influenza virus may be a human or bird influenza virus. The human influenza virus may be virus A, B or C. Influenza viruses carry at least two different surface glycoprotein antigens on the external envelope, hemagglutinin (HA) trimer, consisting of three individual HA monomers, and the neuraminidase (NA) that exists as a tetramer. Both HA and NA cause specific antibody responses due to their high immunogenicity during infection into susceptible cells. There are many influenza A virus subtypes that differ in the nature of HA and NA glycoproteins. 18 HAs (H1 to H18) and 11 NAs (N1 to N11) have been identified. For example, the influenza virus A subtypes may be H5N1, H9N1, H7N7, H2N2, H7N1, H1N1, H1N2, H3N2, H3N8, H4N8, H5N2, H5N3, H5N8, H5N9, H6N5, H7N1, H7N2, H7N3, H7N4, H7N7, H8N4, H9N2, H10N7, H11N7, H11N6, H12N5, H13N6, and H14N5.

Influenza virus B is clearly distinct from influenza A virus and infects humans, especially children.

In an embodiment, the influenza virus may be a virus that is determined to be seasonal and potentially pandemic by the WHO and is distributed by the WHO.

The originally-received influenza virus can be diluted with different dilution factors and each of the diluted samples is passaged twice or more in a cell line adapted to serum-free culture and suspension culture. For primary passage, the influenza virus is diluted with different dilution factors, for example, 1/1 to 1/10,000 or 1/1 to 1/1,000, specifically 1/10, 1/100, and 1/1000 and the cell line adapted to serum-free culture and suspension culture is infected with predetermined amounts of the dilutions. Then, the infected cell line is cultured with stirring at a rate of 10 rpm to 150 rpm at 32° C. to 38° C. for 4 days or less, specifically for 1 day to 3 days. Trypsin may be optionally added at a concentration of 1 μg/mL to 10 μg/mL to the medium. The infected cell line may be optionally cultured in the presence of about 1% to about 10% $CO_2$. The infected cell line may be present at a concentration of about $1.0\times10^4$ cells/ml to about $1.0\times10^8$ cells/ml, specifically about $1.0\times10^5$ cells/ml to about $1.0\times10^7$ cells/ml.

To determine an appropriate time point to collect the influenza virus, the cell viability and HA titer values of the dilutions with different dilution factors are measured 1 day post infection (1DPI) and 2 days post infection (2DPI). The time point to collect the target influenza virus can be determined considering the measured cell viability and HA titer values. Specifically, a culture with a dilution factor where the highest cell viability is obtained is selected from cultures with different dilution factors used for viral infection, provided that when the hemagglutination assay (HA) titers (except for 0) of two or more cultures are different by 4 times or more, a culture with a dilution factor where the highest HA titer is obtained is selected and used for the subsequent passage. It is common practice to select a virus culture having the highest HA titer. It was found in the present invention that cell viability needs to be preferentially taken into consideration to produce a highly infectious virus. Specifically, it is preferred that the cell viability is at least about 50%, at least about 60%, at least about 70%, at least about 80%, at least about 90%, about 100% or in any range between these values. The consideration of cell viability in determining an appropriate time point to collect a target influenza virus is contrary to general technical knowledge. According to the prior art, only the time point at which the highest HA titer is obtained is considered and cell viability is excluded from consideration. Therefore, cultures selected only based on their HA titer often pass their highest cell viability. It was found in the present invention that the selection of a culture having the highest cell viability ensures the production of a highly infectious virus. The HA titer may be 0, at least about 100, at least about 200, at least about 300, at least about 400, at least about 500, specifically at least about 1000, at least about 1100, at least about 1200, at least about 1300, at least about 1400, more specifically at least about 1500 or in any selected range between these values. However, when the hemagglutination assay (HA) titers (except for 0) of two or more cultures are different by 4 times or more, it is preferred to select a culture with a dilution factor where the highest HA titer is obtained. The consideration of the HA titer rather than the cell viability ensures the selection of a culture with the highest infectivity.

It is preferable to select the most optimal results after comparison of the cell viability and HA titer values of the cultures at different dilution factors. For example, a culture having the highest cell viability is preferentially selected from the cultures at different dilution factors, provided that when two or more cultures have the same cell viability, a culture having the higher HA titer may be selected. As another example, a culture having the highest cell viability is preferentially selected from the cultures at different dilution factors, provided that when the HA titer of a culture having a lower cell viability is at least four times higher than that of a culture having the highest cell viability, the culture having a lower cell viability may be selected. As another example, when two or more cultures with different dilution factors have the same highest cell viability, a culture having the higher HA titer may be selected.

The selected primary culture can be directly or serially used for secondary or higher passage. Alternatively, the selected primary culture may be frozen and stored in the temperature range of −50° C. to −80° C., for example, −55° C. to −70° C., before subsequent use, and thereafter, it may be passaged once or more.

For the subsequent secondary passage culture, the primary culture can be diluted with different dilution factors and infect a new cell line adapted to serum-free culture and suspension culture. The secondary passage is performed by the same procedure as described for the primary passage. The dilution factors may be, for example, 1/1 to 1/10,000 but are determined considering the dilution factor where the highest viability and HA titer values are obtained in the primary culture. Thereafter, the cultures with different dilution factors are cultured in the same manner as in the primary culture, their cell viability and HA titer values are measured by the same procedure as described for the primary culture, and a culture having the highest cell viability, which is equal to or higher than that of the primary culture, is selected. The selected culture is collected. The collected culture can be set as an influenza working virus seed stock.

Optionally, the selected culture may be subjected to tertiary or higher passage by the same procedure as described above. The plaque titer of the virus seed stock after the secondary or higher passage can be increased by at least about 10-fold, specifically at least about 100-fold, at least about 200-fold, at least about 300-fold or at least about 400-fold compared to that of the influenza virus before passage, for example, the originally-received influenza virus.

Another aspect of the present invention relates to a method of increasing the infectivity of an influenza working virus seed stock, comprising infecting a cell line adapted to serum-free culture and suspension culture with an influenza vaccine virus, culturing the infected cell line, and further passaging the virus culture in the same cell line to prepare an influenza working virus seed stock wherein a culture with a dilution factor where the highest cell viability is obtained is selected from cultures with different dilution factors used for viral infection, provided that when the hemagglutination assay (HA) titers (except for 0) of two or more cultures are different by 4 times or more, a culture with a dilution factor where the highest HA titer is obtained is selected and used for the subsequent passage. This aspect can be carried out referring to the previous aspect and a description thereof is thus omitted to avoid duplication.

A further aspect of the present invention relates to a method of producing an influenza vaccine, comprising producing an influenza working virus seed stock prepared by the corresponding aspect or an influenza working virus seed stock with increased infectivity by the corresponding aspect on a large scale and attenuating or inactivating the virus seed stock. This aspect enables the production of a virus with increased infectivity on a large scale in a short time compared to the original virus before passage (e.g., the originally-received virus), thus being suitable for mass production of a virus with increased infectivity. The attenuated or inactivated virus may be an inactivated whole virus, a sub-virion (so-called split vaccine) in which purified virus particles are disrupted by a detergent dissolving the lipid envelope or other reagents, or purified HA or NA (subunit vaccine).

Yet another aspect of the present invention relates to an influenza working virus seed stock with increased infectivity prepared by the corresponding method or an influenza vaccine produced by the corresponding method. The infectivity of the influenza working virus seed stock or the influenza vaccine can be increased by at least about 10 times, specifically at least about 10 times, at least about 100 times, at least about 200 times, at least about 300 times or at least about 400 times in plaque titer.

The present invention will be described in detail with reference to the following exemplary embodiments to assist in understanding the present invention. The embodiments of the present invention, however, may be changed into several other forms, and the scope of the present invention should not be construed as being limited to the following embodiments. The embodiments of the present invention are intended to more comprehensively explain the present invention to those skilled in the art.

EXAMPLES

<Example 1> Differences in Infectivity Depending on Cell Viability and HA Titer Upon Culture of Vaccine Virus Strains An MDCK cell line (MDCK Sky3851) adapted to serum-free culture and suspension culture was cultured at 34° C. and 5% $CO_2$ with stirring at a rate of 80 rpm. After cells were grown above a predetermined level through several passages, the medium was replaced with a new one. Thereafter, cells were placed in four 125 mL spinner flasks at a concentration of $3.0\times10^6$ cells/mL to $4.0\times10^6$ cells/mL and the medium was supplemented with trypsin for infection. Influenza vaccine strains in the 2005-2006, 2009-2010, and 2016-2017 seasons were used in this experiment. Virus culture conditions are shown in Table 1.

TABLE 1

<Virus culture conditions>

| Culture conditions | Set value |
|---|---|
| Cell concentration for infection | $3.0\times10^6$-$4.0\times10^6$ cells/mL |
| Culture scale | 125 mL spinner flask |
| Culture period | 2-3 days |
| Stirring rate of spinner flasks | 80 rpm |
| Temperature | 34° C. |
| $CO_2$ concentration | 5% |
| Trypsin concentration | 5 μg/mL |

The influenza virus vaccine strains were diluted 1-1/1,000-fold for virus culture and the cell line was infected with a predetermined amount of each dilution. To determine an appropriate time point to collect each influenza virus, the cell viability and HA titer values of the cultures were measured 1 day or 2 days post infection (DPI). Cultures having different cell viabilities and whose HA titers were different by 2 or 4 times were selected from the cultures with different dilution factors. The results are shown in Table 2.

TABLE 2

<Infectivities of the influenza vaccine strains having different cell viability and HA titer values>

| Influenza vaccine strain | Dilution factor for infection/infection dose | DPI | Cell viability (%) | HA titer (HAU/50 μL) | Plaque titer (pfu/mL) |
|---|---|---|---|---|---|
| NYMC X-283 A | 1/20 μL | 1 | 80 | 256 | $2.20 \times 10^6$ |
| (A/Lisboa/32/2015) | 10/20 μL | | 90 | 128 | $5.40 \times 10^7$ |
| NYMC X-157 | 100/20 μL | 1 | 84 | 512 | $3.51 \times 10^7$ |
| (A/New York/55/2004) | 1000/20 μL | | 92 | 256 | $1.50 \times 10^8$ |
| B/Malaysia/2506/2004 | 10/20 μL | 1 | 91 | 4096 | $6.12 \times 10^8$ |
| | 100/20 μL | | 98 | 2048 | $4.18 \times 10^9$ |
| NYMC X-275 | 1000/20 μL | 2 | 80 | 512 | $4.80 \times 10^7$ |
| (A/Michigan/45/2015) | 10000/20 μL | | 90 | 128 | $2.78 \times 10^7$ |
| NYMC X-175C | 10/20 μL | 2 | 89 | 1024 | $6.70 \times 10^8$ |
| (A/Uruguay/716/2007) | 1000/20 μL | | 94 | 256 | $1.25 \times 10^8$ |
| NYMC BX-35 | 1/20 μL | 2 | 41 | 1024 | $1.40 \times 10^8$ |
| (B/Brisbane/60/2008) | 1000/20 μL | | 82 | 256 | $6.80 \times 10^7$ |

As can be seen from the results in Table 2, the cell viability and HA titer values of the cultures of the influenza vaccine strain NYMC X-283A (A/Lisboa/32/2015) with dilution factors of 1-fold and 10-fold were compared, and as a result, the cell viability (90%) of the culture with a dilution factor of 10-fold was higher than that (80%) of the culture with a dilution factor of 1-fold. Further, the HA titer of the culture with a dilution factor of 10-fold was two times lower than that of the culture with a dilution factor of 1-fold. Plaque assay revealed that the culture with a dilution factor of 10-fold showed a ~24.5 times higher plaque titer despite the two times lower HA titer.

For NYMC X-157 (A/New York/55/2004) and B/Malaysia/2506/2004, the cultures having higher cell viability values showed higher plaque titers despite the two times lower HA titers.

Meanwhile, the cell viabilities and HA titers of the cultures of the influenza vaccine strain NYMC X-275 (A/Michigan/45/2015) with dilution factors of 1000-fold and 10000-fold were compared, and as a result, the cell viability (90%) of the culture with a dilution factor of 10000-fold was higher than that (80%) of the culture with a dilution factor of 1000-fold. Further, the HA titer of the culture with a dilution factor of 10000-fold was four times lower than that of the culture with a dilution factor of 1000-fold. Plaque assay revealed that the culture with a dilution factor of 1000-fold whose HA titer was four times that of the culture with a dilution factor of 10000-fold showed a ~1.7 times higher plaque titer despite lower cell viability.

For the influenza vaccine strains NYMC X-175C (A/Uruguay/716/2007) and NYMC BX-35 (B/Brisbane/60/2008), the cultures whose HA titers were four times higher showed higher plaque titers despite their lower cell viabilities.

<Example 2> Preparation of Influenza Working Virus Seed Stocks (Scale 125 mL Spinner Flasks)

An MDCK cell line (MDCK Sky3851) adapted to serum-free culture and suspension culture was cultured at 34° C. and 5% $CO_2$ with stirring at a rate of 80 rpm. After cells were grown above a predetermined level through several passages, the medium was replaced with a new one. Thereafter, cells were placed in four 125 mL spinner flasks at a concentration of $3.0 \times 10^6$ cells/mL to $4.0 \times 10^6$ cells/mL and the medium was supplemented with trypsin for infection. Influenza vaccine strains in the 2004-2010 seasons were used in this experiment. Primary and secondary virus culture conditions are shown in Table 1.

The influenza virus vaccine strains were diluted 1-1/1,000-fold for primary virus culture and the cell line was infected with a predetermined amount of each dilution. To determine an appropriate time point to collect each influenza virus, the cell viability and HA titer values of the cultures were measured 1 day and 2 days post infection (DPI). Cultures having the highest cell viabilities were selected from the cultures with different dilution factors. The results are shown in Table 3. In this example, cultures whose HA titers (except for 0) were different by 4 times were not found. The selected primary cultures were collected after 2DPI, centrifuged at 3,000 rpm for 10 min, divided into small portions (each 1 mL), and stored at ≤−70° C. The culture in one of the vials was defrosted and diluted 1-1/10,000-fold, infected for secondary virus passage culture, and cell viability and HA titer thereof were measured 1DPI and 2DPI in the same manner as in the primary passage culture. Cultures having the highest cell viabilities were selected from the cultures with different dilution factors. The results are shown in Table 3. In this example, cultures whose HA titers (except for 0) were different by 4 times were not found. The secondary cultures were finally selected after 2DPI, collected, centrifuged at 3,000 rpm for 10 min, divided into small portions (each 1 mL), and stored at ≤−70° C., which were set as influenza working virus seed stocks.

TABLE 3

<HA titer and cell viability values of the influenza vaccine strains in the 2004-2010 seasons>

| Influenza vaccine strains | Number of cultures | Dilution factor for infection/Infection dose | 1DPI Cell viability (%) | 1DPI HA titer (HAU/ 50 μL) | 2DPI Cell viability (%) | 2DPI HA titer (HAU/ 50 μL) |
| --- | --- | --- | --- | --- | --- | --- |
| IVR-116 (A/New | Primary culture | 1000/20 μL | 100 | 0 | 71 | 1024 |
| Caledonia/20/99) | Secondary culture | 10000/20 μL | 99 | 32 | 80 | 1024 |
| IVR-145 (A/Solomon | Primary culture | 10/20 μL | 100 | 256 | 73 | 512 |
| Islands/3/2006) | Secondary culture | 10000/20 μL | 96 | 0 | 75 | 512 |
| IVR-148 | Primary culture | 1000/20 μL | 100 | 512 | 83 | 2048 |
| (A/Brisbane/59/2007) | Secondary culture | 10000/20 μL | 99 | 256 | 84 | 1024 |
| NYMC X-147 | Primary culture | 1000/20 μL | 100 | 0 | 83 | 256 |
| (A/Wyoming/03/2003) | Secondary culture | 10000/20 μL | 100 | 0 | 91 | 256 |
| NYMC X-161B | Primary culture | 1000/20 μL | 100 | 0 | 94 | 2048 |
| (A/Wisconsin/67/2005) | Secondary culture | 10000/20 μL | 100 | 16 | 85 | 2048 |
| NYMC X-175C | Primary culture | 1000/20 μL | 99 | 0 | 93 | 1024 |
| (A/Uruguay/716/2007) | Secondary culture | 10/20 μL | 99 | 512 | 89 | 1024 |
| B/Florida/4/2006 | Primary culture | 1/20 μL | 98 | 2048 | 7 | 4096 |
|  | Secondary culture | 1000/20 μL | 95 | 0 | 77 | 1024 |

Plaque assay was conducted to determine the infectivity of supernatants collected at 2DPI of the primary culture and the secondary culture. The results are shown in Table 4. The influenza vaccine strains were serially passaged twice in the MDCK cell line (MDCK Sky3851) adapted to serum-free culture and suspension culture. As a result, the plaque titers of the supernatants were found to be ~10-1,000 times higher than those of the influenza vaccine strains.

TABLE 4

<Plaque titers of the influenza vaccine strains collected after culture>

| Subtype | Season | Candidate influenza vaccine virus | Plaque titer (pfu/mL) Influenza vaccine strain | Plaque titer (pfu/mL) Primary culture | Plaque titer (pfu/mL) Secondary culture |
| --- | --- | --- | --- | --- | --- |
| A/H1N1 | 2006-2007 | IVR-116 (A/New Caledonia/20/99) | $1.84 \times 10^7$ | $1.60 \times 10^9$ | $3.04 \times 10^9$ |
|  | 2007-2008 | IVR-145 (A/Solomon Islands/3/2006) | $1.74 \times 10^7$ | $4.64 \times 10^8$ | $2.36 \times 10^9$ |
|  | 2009-2010 | IVR-148 (A/Brisbane/59/2007) | $1.38 \times 10^8$ | $1.82 \times 10^9$ | $1.14 \times 10^9$ |
| A/H3N2 | 2004-2005 | NYMC X-147 (A/Wyoming/03/2003) | $1.74 \times 10^5$ | $3.74 \times 10^8$ | $2.44 \times 10^8$ |
|  | 2007-2008 | NYMC X-161B (A/Wisconsin/67/2005) | $2.82 \times 10^6$ | $2.06 \times 10^9$ | $2.08 \times 10^9$ |
|  | 2009-2010 | NYMC X-175C (A/Uruguay/716/2007) | $1.54 \times 10^7$ | $5.86 \times 10^8$ | $6.70 \times 10^8$ |
| B | 2008-2009 | B/Florida/4/2006 | $7.40 \times 10^6$ | $8.20 \times 10^8$ | $3.48 \times 10^9$ |

<Example 3> Preparation of Influenza Working Virus Seed Stocks (Scale 3 L Spinner Flasks)

An MDCK cell line (MDCK Sky3851) adapted to serum-free culture and suspension culture was cultured at 34° C. and 5% $CO_2$ with stirring at a rate of 80-100 rpm. After cells were grown above a predetermined level through several passages, the medium was replaced with a new one. Thereafter, cells were placed in four 125 mL spinner flasks at a concentration of $3.0 \times 10^6$ cells/mL to $4.0 \times 10^6$ cells/mL for primary virus culture and in four 3 L spinner flasks at a concentration of $3.0 \times 10^6$ cells/mL to $4.0 \times 10^6$ cells/mL for secondary virus culture, and the medium was supplemented with trypsin for infection. Influenza vaccine strains in the 2013-2017 seasons were used in this experiment. Primary and secondary virus culture conditions are shown in Table 5.

TABLE 5

<Primary and secondary virus culture conditions>

| Culture conditions | Set values for primary virus culture | Set values for secondary virus culture |
|---|---|---|
| Cell concentration for infection | $3.0 \times 10^6$-$4.0 \times 10^6$ cells/mL | $3.0 \times 10^6$-$4.0 \times 10^6$ cells/mL |
| Culture scale | 125 mL spinner flask | 3 L spinner flask |
| Culture period | 2-3 days | 2-3 days |
| Stirring rate of spinner flasks | 80 rpm | 100 rpm |
| Temperature | 34° C. | 34° C. |
| $CO_2$ concentration | 5% | 5% |
| Trypsin concentration | 5 µg/mL | 5 µg/mL |

1DPI and 2DPI cultures after secondary virus culture were obtained in the same manner as in Example 2. The cultures were centrifuged at 3,000 rpm for 10 min, divided into small portions (each 1 mL), and stored at ≤−70° C., which were set as influenza working virus seed stocks. The cell viability and HA titer values of the influenza vaccine strains were measured at 1DPI and 2DPI of the primary and secondary passage culture. The results are shown in Table 6.

TABLE 6

<HA titer and cell viability values of the influenza vaccine strains in the 2013-2017 seasons>

| Influenza vaccine strains | Number of cultures | Dilution factor for infection/Infection dose | 1DPI Cell viability (%) | 1DPI HA titer (HAU/50 µL) | 2DPI Cell viability (%) | 2DPI HA titer (HAU/50 µL) |
|---|---|---|---|---|---|---|
| NIB-74xp (A/Christchurch/16/2010) | Primary culture | 10/20 µL | 100 | 1024 | — | — |
|  | Secondary culture | 100/333 µL | 99 | 2048 | — | — |
| NYMC X-223A (A/Texas/50/2012) | Primary culture | 1/20 µL | 99 | 1024 | — | — |
|  | Secondary culture | 10/333 µL | 99 | 2048 | — | — |
| NYMC X-247 (A/Switzerland/9715293/2013) | Primary culture | 1/20 µL | 94 | 1024 | — | — |
|  | Secondary culture | 10/333 µL | 97 | 1024 | — | — |
| NYMC X-263 (A/Hong Kong/4801/2014) | Primary culture | 100/20 µL | 100 | 0 | 89 | 1024 |
|  | Secondary culture | 100/333 µL | 100 | 512 | 95 | 1024 |
| NIB-93 (A/Hong Kong/7127/2014) | Primary culture | 1,000/20 µL | 100 | 0 | 85 | 512 |
|  | Secondary culture | 1,000/333 µL | 100 | 0 | 89 | 512 |
| B/Massachusetts/2/2012 | Primary culture | 10/20 µL | 99 | 0 | 95 | 2048 |
|  | Secondary culture | 100/333 µL | 100 | 0 | 85 | 4096 |
| NYMC BX-35 (B/Brisbane/60/2008) | Primary culture | 1/20 µL | 99 | 0 | 41 | 1024 |
|  | Secondary culture | 10/333 µL | 98 | 0 | 88 | 2048 |
| B/Phuket/3073/2013 | Primary culture | 100/20 µL | 100 | 0 | 97 | 2048 |
|  | Secondary culture | 1,000/333 µL | 100 | 0 | 75 | 4096 |

Plaque assay was conducted on the final cultures to confirm the infectivity of the influenza working virus seed stocks listed in Table 6. The results are shown in Table 7. Similarly to the results in Table 4 (Example 2), most of the plaque titers of the influenza working virus seed stocks after the two successive passages in the MDCK cell line (MDCK Sky3851) adapted to serum-free culture and suspension culture were $\geq 1.00 \times 10^8$ pfu/mL.

TABLE 7

<Plaque titers of the influenza working virus seed stocks in the 2013-2017 seasons>

| Subtype | Season | Candidate influenza vaccine virus | Plaque titer (pfu/mL) |
|---|---|---|---|
| A/H1N1 | 2013-2017 | NIB-74xp (A/Christchurch/16/2010) | $1.01 \times 10^9$ |
| A/H3N2 | 2013-2015 | NYMC X-223 A (A/Texas/50/2012) | $3.31 \times 10^8$ |
|  | 2015-2016 | NYMC X-247 (A/Switzerland/9715293/2013) | $1.70 \times 10^7$ |

TABLE 7-continued

<Plaque titers of the influenza working virus seed stocks in the 2013-2017 seasons>

| Subtype | Season | Candidate influenza vaccine virus | Plaque titer (pfu/mL) |
|---|---|---|---|
| | 2016-2017 | NYMC X-263 (A/Hong Kong/4801/2014) | $1.20 \times 10^9$ |
| | | NIB-93 (A/Hong Kong/7127/2014) | $3.30 \times 10^8$ |
| B | 2013-2015 | B/Massachusetts/2/2012 | $1.37 \times 10^9$ |
| | | NYMC BX-35 (B/Brisbane/60/2008) | $2.70 \times 10^8$ |
| | 2015-2017 | B/Phuket/3073/2013 | $2.60 \times 10^9$ |

<Example 4> Sequencing of the Influenza Working Virus Seed Stocks

A determination was made as to whether there were changes in the antigenicity of hemagglutinin (HA) and neuraminidase (NA) as major surface antigens after the influenza vaccine strains were passaged three times in an MDCK cell line adapted to serum-free culture and suspension culture. To this end, changes in the sequences of the antigens were identified. The vaccine strains were passaged twice in the same manner as in Example 2 and was passaged once more (a total of three times). Thereafter, RNA was extracted from each virus using a PureLink Viral RNA/DNA kit (Invitrogen) and the HA and NA genes were selectively amplified by PCR with a SUPERSCRIPTIII ONE-STEP RT-PCR system (Invitrogen) and primers specific for the HA and NA genes of the virus strain. Subsequently, impurities were removed from the PCR products using a QIAquick PCR purification kit. DNA sequencing was performed with an ABI PRISM 3130x/genetic analyzer and assembly of the sequence data was done using SeqMan Pro and MegAlign in the DNA STAR, Lasergene 8.1 program.

TABLE 8

<Reference virus strains used for sequencing>

| Subtype | Virus strain for WVSS preparation | Reference virus strain |
|---|---|---|
| A/H1N1 | NYMC X-181A (A/California/07/2009) | NYMC X-181A (A/California/07/2009) |
| A/H3N2 | NYMC X-187 (A/Victoria/210/2009) | NYMC X-187 (A/Victoria/210/2009) |
| B/Victoria | NYMC BX-35 (B/Brisbane/60/2008) | NYMC BX-35 (B/Brisbane/60/2008) |

The results in Table 8 demonstrate that even after all influenza vaccine strains of A/H1N1, A/H3N2, and B subtypes were passaged three times in the MDCK cell line adapted to serum-free culture and suspension culture, no changes in the sequences of the HA and NA genes as major surface antigens were caused. In conclusion, the antigenicity of the antigens was maintained unchanged.

The invention claimed is:

1. A method of preparing an influenza working virus seed stock, the method comprising:
 a) infecting a cell line adapted to serum-free culture and suspension culture with an influenza vaccine virus such that the infecting is carried out at a plurality of dilution factors, relative to a proportion of the influenza vaccine used to perform the infecting, to obtain a plurality of infected cell lines at different dilution factors;
 b) culturing the plurality of infected cell lines, to obtain a plurality of virus cultures at the different dilution factors;
 c) measuring cell viability of each of the plurality of virus cultures, and performing a hemagglutination assay (HA) on each of the plurality of virus cultures;
 d) selecting one of the plurality of virus cultures as a selected virus culture based on Condition 1 or Condition 2:
 Condition 1: if measured HA titers (except for HA titers of 0) of at least two of the plurality of virus cultures are different by a factor of 4 times or more, then the selected virus culture is a virus culture with a dilution factor having a highest measured HA titer, or
 Condition 2: if Condition 1 is not satisfied, then the selected virus culture is a virus culture with a dilution factor having a highest measured cell viability; and
 e) further passaging the selected virus culture in the same cell line at least once.

2. The method according to claim 1, wherein the cell line adapted to serum-free culture and suspension culture is an MDCK cell line.

3. The method according to claim 2, wherein the MDCK cell line is MDCK Sky1023 (DSM ACC3112), MDCK Sky10234 (DSM ACC3114) or MDCK Sky3851 (DSM ACC3113).

4. The method according to claim 1, wherein the plurality of infected cell lines are cultured with stirring at a rate of 10 rpm to 150 rpm at 32° C. to 38° C. for 1 day to 3 days.

5. The method according to claim 1, wherein the selected virus culture is serially passaged twice or more, or is frozen and stored in the temperature range of −50° C. to −80° C. and is passaged twice or more.

6. The method according to claim 1, wherein the measured cell viability of the selected virus culture is at least 50%.

7. The method according to claim 6, wherein the measured hemagglutination assay (HA) titer of the selected virus culture is 0 or at least about 100.

8. The method according to claim 1, wherein the plurality of dilution factors range from 1/1 to 1/10,000.

9. A method of producing an influenza vaccine, the method comprising producing an influenza working virus seed stock by the method according to claim 1 and attenuating or inactivating the influenza working virus seed stock.

10. The method according to claim 9, wherein the infectivity of the influenza working virus seed stock is higher than that of the influenza vaccine virus before passage.

11. A method of increasing the infectivity of an influenza working virus seed stock, the method comprising:
 a) infecting a cell line adapted to serum-free culture and suspension culture with an influenza vaccine virus such that the infecting is carried out at a plurality of dilution factors, relative to a proportion of the influenza vaccine used to perform the infecting, to obtain a plurality of infected cell lines at different dilution factors;
 b) culturing the plurality of infected cell lines, to obtain a plurality of virus cultures at the different dilution factors;
 c) measuring cell viability of each of the plurality of virus cultures, and performing a hemagglutination assay (HA) on each of the plurality of virus cultures;
 d) selecting one of the plurality of virus cultures as a selected virus culture based on Condition 1 or Condition 2:
 Condition 1: if measured HA titers (except for HA titers of 0) of at least two of the plurality of virus cultures are different by a factor of 4 times or more, then the selected virus culture is a virus culture with a dilution factor having a highest measured HA titer, or Condition 2: if Condition 1 is not satisfied, then the selected virus culture is a virus culture with a dilution factor having a highest measured cell viability; and e) further passaging the selected virus culture in the same cell line to prepare an influenza working virus seed stock at least once.

12. The method according to claim 11, wherein the cell line adapted to serum-free culture and suspension culture is an MDCK cell line.

* * * * *